United States Patent [19]

Gold

[11] 4,291,048

[45] Sep. 22, 1981

[54] METHOD OF TREATING TUMORS AND CANCEROUS CACHEXIA WITH L-TRYPTOPHAN

[76] Inventor: Joseph Gold, 127 Edgemont Dr., Syracuse, N.Y. 13214

[21] Appl. No.: 44,303

[22] Filed: May 31, 1979

Related U.S. Application Data

[63] Continuation of Ser. No. 922,502, Jul. 6, 1978, abandoned, which is a continuation-in-part of Ser. No. 756,648, Jan. 4, 1977, abandoned, which is a continuation of Ser. No. 558,254, Mar. 14, 1975, abandoned, which is a continuation of Ser. No. 372,097, Jun. 21, 1973, abandoned, which is a continuation-in-part of Ser. No. 198,995, Nov. 15, 1971, abandoned, which is a continuation-in-part of Ser. No. 861,176, Sep. 25, 1969, abandoned.

[51] Int. Cl.³ .............................................. A61K 31/40

[52] U.S. Cl. ................................................... 424/274
[58] Field of Search ....................................... 424/274

[56] References Cited

PUBLICATIONS

Chemical Abstracts 69: 50495k (1968).
Chemical Abstracts 72: 109650z (1970).
Dyer, An Index of Tumor Chemotherapy, NIH, Mar. 1949, pp. 10, 11 & 143.

Primary Examiner—Jerome D. Goldberg
Attorney, Agent, or Firm—Henry P. Stevens

[57] ABSTRACT

A method of inhibiting the growth of tumors by inhibiting gluconeogenesis and thereby interrupting the process of cachexia by the internal administration of compositions containing L-tryptophan to mammals so afflicted is disclosed.

1 Claim, No Drawings

METHOD OF TREATING TUMORS AND CANCEROUS CACHEXIA WITH L-TRYPTOPHAN

CROSS REFERENCE TO RELATED APPLICATIONS

This application is a continuation of U.S. Ser. No. 922,502 filed July 6, 1978 now abandoned which in turn was a continuation-in-part of U.S. Ser. No. 756,648 filed Jan. 4, 1977 now abandoned which in turn was a continuation of U.S. Ser. No. 558,254 filed Mar. 14, 1975 now abandoned which in turn was a continuation of U.S. Ser. No. 372,097 filed June 12, 1973 now abandoned which in turn was a continuation-in-part of U.S. Ser. No. 198,995 filed Nov. 15, 1971 now abandoned which in turn was a continuation-in-part of U.S. Ser. No. 861,176 filed Sept. 25, 1969 and now abandoned.

BACKGROUND OF THE INVENTION

Many different types of chemical compounds have been used in the past to treat tumors in mammals including humans. Examples of such compounds are the nitrogen mustards, estrogen, insulin, tolbutamide, hydrazine sulfate, fluorouracil and the biguanides. The exact mode of action encountered in such chemotherapy has never been firmly established and the degree of successful therapy has been nominal at best.

During the past 4 decades, it has been generally recognized that carbohydrate metabolism in the neoplastic process has some relationship to cancerous growths, but its exact role has not been clearly defined. It is now proposed that in cancer subjects, gluconeogenesis together with glycolysis constitutes a type of metabolic circuit whereby the body is depleted of energy reserves, resulting in cachexia, the latter being the process of gradual bodily deterioration and weight loss in the presence of a flourishing tumor. The process of cachexia is dependent on the free functioning of the metabolic pathways of gluconeogenesis in which energy from normal cells is expended upon gluconeogenic precursors (compounds containing 2-5 carbon atoms) in their synthesis to glucose (6 carbon atoms). A more detailed explanation of the carbohydrate mechanisms which are operative in such metabolism will be hereinafter more fully discussed. At this point, it is sufficient to state that if the process of gluconeogenesis can be inhibited, and preferably without interfering with other normal metabolic processes, including glycolysis, a marked reduction in energy expended or drained from normal body cells would take place, leading to an inhibition of cachexia; and at the same time a resulting decrease or reduction in the tumor growth rate. It has been found that under abnormal conditions large amounts of glucose can be synthesized via gluconeogenesis in amounts far in excess of the total minimum daily body requirement for glucose. The resulting energy drawn from normal tissues caused by such a great augmentation in gluconeogenesis (such as the recycling of lactic acid to glucose) can be tremendous, utilizing the equivalent of at least six molecules of adenosine triphosphate (ATP) per new glucose molecule formed.

SUMMARY OF THE INVENTION

This invention is based upon the discovery that the administration of L-tryptophan to mammals including humans afflicted with various tumors such as carcinoma, sarcoma and melanoma will interrupt gluconeogenesis and thereby halt cachexia by imposing a restriction on the availability of glucose to the tumor cells with an attendant reduction in tumor growth. The treatment of humans afflicted with cancerous cachexia is an integral aspect of the present invention in that the cachexia can be treated by continuous use of L-tryptophan even in the absence of tumor reduction.

GENERAL DESCRIPTION OF THE INVENTION

In the normal mammal, carbohydrate (glucose) is degraded via the Embden-Meyerhof pathway to yield a 3-carbon fragment, pyruvate, which enters the tri-carboxylic acid cycle (respiration) as active-acetate and is then oxidized to carbon dioxide and water. However, where a tumor exists in such a mammal, the glycolysis proceeds from pyruvate to yield lactate or lactic acid. Two primary distinctions of importance exist between tumor tissue and normal tissue with respect to the glycolytic process. First, the tumor cells produce lactate, while the normal cells proceed from pyruvate to active-acetate; and second, the tumor tissue's anaerobic glycolytic process is at least 4 to 5 times greater than the glycolytic rate of normal cells. Anaerobic glycolysis yields a net formation of 2 ATP per glucose molecule, while the oxidative respiration pathway produces some 30 ATP per glucose molecule.

In the gluconeogenesis process, which is approximately the reverse of the glycolytic process, mainly glucose but also other hexose derivatives are synthesized from non-carbohydrates, including amino acids, oxaloacetate, lactate and others. One primary exception to the general reverse pathways exists in the conversion of pyruvate to phosphoenolpyruvate (phosphopyruvate or PEP). In glycolysis, phosphoenolpyruvate (PEP) proceeds directly to pyruvate, but in gluconeogenesis, the pyruvate is first converted to oxaloacetate by the enzyme pyruvate carboxylase. The oxaloacetate is then converted to phosphoenolpyruvate (PEP) by means of the enzyme phosphoenolpyruvate carboxykinase (PEP carboxykinase) and the PEP then proceeds back to glucose.

It was previously mentioned that in the anaerobic breakdown of glucose to lactic acid a net 2 ATP per glucose molecule is yielded to the tumor. However, synthesis of glucose from the resulting lactic acid via gluconeogenesis requires the utilization of the equivalent of at least 6 ATP (7 ATP with glycogen), derived from normal tissues. Thus, at least 8 ATP are "lost" to the body economy each time the above-described recycling occurs, broken down as 2 ATP to the tumor and 6 ATP from the rest of the body. Such a metabolic circuit, i.e., the utilization of glucose by a malignancy to produce small amounts of energy for its own needs, at the expense of large amounts of energy from the rest of the body is believed to be the thermodynamic means by which the tumor flourishes while the body wastes away. Even normal, appearing tissue of origin adjacent to tumor tissue produces high rates of glycolysis thereby contributing to cachexia via augmented lactate production.

From the foregoing, it is apparent that if the gluconeogenic process can be inhibited, the result will be an interruption of the process of cachexia as well as an inhibition of primary tumor growth due to augmentation of the body's resistance and a lesser availability of glucose to feed the tumor.

Thus, in its broadest aspect, the present invention contemplates the interruption of gluconeogenesis as a means for treatment of tumors. More specifically, such interruption should take place so that it does not interfere with the normal glycolysis process, the latter apparently required for certain body functions. Interruption of gluconeogenesis can be combined with a low carbohydrate diet to thereby restrict the availability of glucose to the tumor cell. If the conversion steps of oxaloacetate to phosphoenolpyruvate (PEP) can be blocked, gluconeogenesis is inhibited. However, since oxaloacetate is not an intermediate in the glycolytic process, the latter may proceed in a normal fashion. Also, since this step occurs prior to the entry in the gluconeogenic process of lactate, amino acids and other important precursors, the energy drain above discussed, together with cachexia is effectively impeded. In other words, a block at PEP carboxykinase, the enzyme which converts oxaloacetate to PEP, retards gluconeogenesis by inhibiting virtually all precursors (with the exception of glycerol) from which glucose can be synthesized without interfering with the normal tissues which depend on glycolysis for a portion of their supply of energy.

Gluconeogenesis inhibition at the above-mentioned enzymic reaction site results from the administration of L-tryptophan which is quite soluble in water or alcohol and may be readily dissolved or suspended in sterile, aqueous, isotonic, saline solution and conveniently administered orally or parenterally to mammals as well as humans evincing symptoms of tumor growth. To prepare other suitable compositions, L-tryptophan can be mixed separately with liquid carriers such as vegetable oils, benzyl alcohol, propylene glycol and the like to form a solution, suspension or emulsion containing preferably from 3% to 7% by weight of active ingredient. If desired, other substances such as preserving agents, buffers, wetting or emulsifying agents and salts can be added. L-tryptophan can also be formulated with solid carriers such as milk sugar, acacia, corn starch, talc, stearic acid or magnesium stearate and compressed into tablets for oral administration. Such tablets can be enteric coated with shellac or cellulose acetate phthalate in a manner well known to those skilled in the tablet making art. In addition, L-tryptophan per se or admixed with any of the liquid or solid carriers hereinbefore enumerated can be sealed in a gelatin capsule for oral or rectal use.

Effective dosages will vary depending upon the route of administration. In general, a dosage equal to about one-half of the $LD_{50}$ will produce good inhibition of tumor growth. Since L-tryptophan is substantially non-toxic, dosages on the order of 400 to 1600 mg/kg daily of body weight are satisfactory, by all routes of administration such as intravenously, intraperitoneally, orally or rectally. However, even lower dosages of about 4 grams per day have been found to be effective.

THE PREFERRED EMBODIMENTS

EXAMPLE 1

In this series of tests, L-tryptophan was used to ascertain tumor inhibiting effects. The subjects used were growing female rats weighing about 70 grams each. Five rats were used at each of the three dosage levels hereinafter described and ten rats served as controls. In making the tests, the standardized routine according to the Cancer Chemotherapy National Service Center of the U.S. Department of Health, Education and Welfare was followed.

On day 1, five million cells of Walker 256 intramuscular carcinoma in a volume of 0.2 ml were injected into one thigh of each rat. On days 3,4,5 and 6, according to the conventional testing procedure, L-tryptophan was injected intraperitoneally in dosages of 1600 mg/kg, 800 mg/kg and 400 mg/kg respectively for the three dosage levels. The L-tryptophan was prepared as a suspension in a medium consisting of water, lecithin, carboxymethylcellulose and a surfactant adjusted to a pH of 6.7, which was found to be extremely stable. The control rats were injected with the suspending vehicle alone, at a pH of 6.7. The volumes of the injection per kilogram of body weight were the same for the test and control subjects.

The animals were sacrificed on day 7, and both lower extremities were removed. The difference in weight between the tumor thigh and the contralateral thigh was used as the weight of the tumor. Tumor size was also measured in terms of average tumor diameter. The animals were weighed before and after each test as an index of possible drug toxicity. All animals were maintained on standard laboratory chow and water. Tumor inhibition was measured as T/C or the ratio of the tumor weight of the treated animals divided by the tumor weight of the control animals.

At a dosage of 1600 mg/kg of L-tryptophan, the tumor response in the treated group was 6.1 grams compared to a tumor response in the control (non-treated) group of 11.8 grams, which is a tumor inhibition of 48%. The net animal weight gain in both the control and treated groups was 13.5 grams, indicating no toxicity at the dosage level employed. In terms of average tumor diameter at this dosage, there was a 52% reduction in growth, which was shown to be statistically significant. With L-tryptophan daily dosages of 800 and 400 mg/kg, the treated animals showed a T/C ratio of 0.52 and 0.64 respectively, or a tumor inhibition of 48% and 36% respectively.

Similar tests with other amino acids such as histidine, proline, leucine, glutamic acid and phenylalanine at dosages of 400, 800 and 1600 mg/kg of body weight showed no inhibiting effect on the growth of implanted Walker 256 carcinoma. Thus, the action of L-tryptophan is specific and not related to an amino acid imbalance brought about by the administration of simply any amino acid in large dosages. The primary mechanism of action of L-tryptophan is presumed due to its inhibition of the enzyme phosphoenolpyruvate carboxykinase (PEP carboxykinase) which results in a block to gluconeogenesis and retardation of cachexia.

EXAMPLE 2

Ten milligrams of B-16 melanoma tumor was implanted in bits in each of 15 black mice used as a control group. Similarly, three different dosage levels of L-tryptophan were used to treat 15 such mice in each test group. On day 1, all the animals were implanted with the melanoma. On days 4-7, the mice were injected intraperitoneally with the L-tryptophan suspension described in Example 1 at the dosages shown in the table below. On day 8, all the mice were sacrificed and their tumors excised and weighed with the following results

| Dosage in Grams/kg | Average Tumor Weight in Milligrams | Percent Inhibition |
| --- | --- | --- |
| 1.2 | 102 | 40 |

| Dosage in Grams/kg | Average Tumor Weight in Milligrams | Percent Inhibition |
|---|---|---|
| 0.8 | 100 | 41 |
| 0.4 | 104 | 38 |
| 0 (control) | 169 | — |

EXAMPLE 3

A 60 year old patient afflicted with lipomyxosarcoma was placed on a regimen of two grams of L-tryptophan twice a day and 2400 calorie diet with only 25 calories of carbohydrate provided. He had three nodules along the scar of a previous surgical operation in which a 1700 gram mass was removed from his left upper quadrant. These nodules measured from 1 to 3.5 centimeters in diameter after growing rapidly for six weeks from an impalpable state prior to treatment. During the six weeks on the tryptophan regimen, the growth of the nodules was inhibited although they did not regress and the patient's weight remained constant. Upon further treatment with adriamycin (an antiobiotic with antitumor properties) and cyclophosphamide (an experimental antitumor agent), the nodules nearly doubled in size and the patient eventually died due to the subsequent enlargement of the nodules.

Beneficial effects similar to those described in the foregoing examples are obtained when L-tryptophan at the doses previously set forth is administered intramuscularly, intravenously, rectally or orally in a manner well known to those skilled in the medical and pharmaceutical arts.

I claim:

1. A method of treating a transplanted B-16 melanoma which comprises parenterally administering to a mammal so afflicted L-tryptophan in an effective amount to inhibit the growth of said tumor.

* * * * *